US005786451A

United States Patent [19]

Thirkill

[11] Patent Number: 5,786,451

[45] Date of Patent: Jul. 28, 1998

[54] 23 KD HUMAN RETINAL CAR ANTIGEN

[75] Inventor: Charles E. Thirkill, Davis, Calif.

[73] Assignee: The Regents of the University of California, Oakland, Calif.

[21] Appl. No.: 820,051

[22] Filed: Mar. 18, 1997

Related U.S. Application Data

[63] Continuation of Ser. No. 343,827, Nov. 22, 1994, abandoned, which is a continuation of Ser. No. 874,843, Apr. 28, 1992, abandoned.

[51] Int. Cl.$^6$ .......................... C07K 14/435; C12H 15/09

[52] U.S. Cl. .......................... 530/350; 435/69.1; 435/325; 536/23.5

[58] Field of Search .......................... 530/350, 412; 435/69.1, 325; 536/23.5

[56] References Cited

U.S. PATENT DOCUMENTS 5,405,749 4/1995 Polans .......................... 435/7.23

OTHER PUBLICATIONS

Darnell et al., Molecular Cell Biology, pp. 54, 55, and 258–260, Scientific American Books, 1986.

The Cancer–Associated Retinopathy antigen is Recoverin–like Protein, by Charles E. Thirkill, et al., *Investigative Ophthalmology & Visual Science*, vol. 33, No. 10, Sep. 1992, pp. 2768–2772.

Sambrook et al., "Molecular Cloning, A Laboratory Manual", Cold Spring Harbor Laboratory Press, vol. 3 pp. 16.2–16.31 1989.

Young et al., Proc. Natl. Acad. Sci., vol. 80, 1194–1198, 1983.

Thirkill, Charles E. et al., "Antibody Indications of Secondary and Superinposed Retinal Hypersensitivity in Retinitis Pigmentosa." J. Opthalmology. 112:132–137 (1991).

Jacobson, Daniel M. et al., "A Clinical Triad to Diagnose Paraneoplastic Retinopathy." Annals of Neurology, 28:162–167 (1990).

Thirkill, Charles E. et al., "Cancer–Associated Retinopathy (CAR Syndrome) with Antibodies Reacting with Retinal, Optic–Nerve, and Cancer Cells." New England J. of Medicine 321:1589–1594 (1989).

Thirkill, Charles E. et al., "Circulating and Localized Immune Complexes in Experimental Mycoplasma–Induced Arthritis–Associated Ocular Inflammation." Infection and Immunity. 60:401–405(1992).

Keltner, John L. et al., "Management and Monitoring of Cancer–Associated Retinopathy." Arch Ophthalmol. 110:48–53 (1992).

Thirkill, Charles E. et al., "Cloning and Sequencing of the 23 Kd Retinal Car Antigen." ARVO 1310–48(1991).

Dizhoor, Alexander M. et al, "Recoverin: A Calcium Sensitive Activator of Retinal Rod Guanylate Cyclase." Science. 915–918(Feb. 1991).

Polans, Arthur S. et al. "A Photoreceptor Calcium Binding Protein Is Recognized by Autoantibodies Obtained from Patients with Cancer–associated Retinopathy" J. Cell Biology 112:981–989(1991).

Thirkill, Charles E., et al. "Cancer–Associated Retinopathy" Arch–Opthalmol 105:372–375(1987).

*Primary Examiner*—Sally P. Teng
*Attorney, Agent, or Firm*—Hana Verny

[57] ABSTRACT

A purified polypeptide having an amino acid sequence SEQ ID NO: 1, which is a human retinal cancer-associated retinopathy antigen capable of selectively binding to antibodies present in a body fluid of a human patient afflicted with cancer associated retinopathy. A recombinant 23 kDa polypeptide which is recombinantly synthesized human retinal cancer-associated retinopathy antigen having an amino acid sequence SEQ ID NO: 1.

2 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 200 amino acids
( B ) TYPE: amino acid
( C ) STRANDEDNESS: double
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: human CAR antigen ( x i ) SEQUENCE DESCRIPTION: SEQ ID NO:1:

```
Met Gly Asn Ser Lys Ser Gly Ala Leu Ser Lys Glu Ile Leu Glu Glu
1               5                   10                  15

Leu Gln Leu Asn Thr Lys Phe Ser Glu Glu Glu Leu Cys Ser Trp Tyr
            20                  25                  30

Gln Ser Phe Leu Lys Asp Cys Pro Thr Gly Arg Ile Thr Gln Gln Gln
        35                  40                  45

Phe Gln Ser Ile Tyr Ala Lys Phe Phe Pro Thr Pro Thr Pro Lys Ala
    50                  55                  60

Tyr Ala Gln His Val Phe Arg Ser Phe Asp Ser Asn Leu Asp Gly Thr
65                  70                  75                  80

Leu Asp Phe Lys Glu Tyr Val Ile Ala Leu His Met Thr Thr Ala Gly
                85                  90                  95

Lys Thr Asn Gln Lys Leu Glu Trp Ala Phe Ser Leu Tyr Asp Val Asp
            100                 105                 110
```

-continued

| | | | | | | | | | | | | | | | |
|---|---|---|---|---|---|---|---|---|---|---|---|---|---|---|---|
| Gly | Asn | Gly | Thr | Ile | Ser | Lys | Asn | Glu | Val | Leu | Glu | Ile | Val | Met | Ala |
| | | 115 | | | | | 120 | | | | | 125 | | | |
| Ile | Phe | Lys | Met | Ile | Thr | Pro | Glu | Asp | Val | Lys | Leu | Leu | Pro | Asp | Asp |
| | 130 | | | | | 135 | | | | | 140 | | | | |
| Glu | Asn | Thr | Pro | Glu | Lys | Arg | Ala | Glu | Lys | Ile | Trp | Lys | Tyr | Phe | Gly |
| 145 | | | | | 150 | | | | | 155 | | | | | 160 |
| Lys | Asn | Asp | Asp | Asp | Lys | Leu | Thr | Glu | Lys | Glu | Phe | Ile | Glu | Gly | Thr |
| | | | | 165 | | | | | 170 | | | | | 175 | |
| Leu | Ala | Asn | Lys | Glu | Ile | Leu | Arg | Leu | Ile | Gln | Phe | Glu | Pro | Gln | Lys |
| | | | 180 | | | | | 185 | | | | | 190 | | |
| Val | Lys | Glu | Lys | Met | Lys | Asn | Ala | | | | | | | | |
| | | 195 | | | | | 200 | | | | | | | | |

( 2 ) INFORMATION FOR SEQ ID NO:2:

( i ) SEQUENCE CHARACTERISTICS:
( A ) LENGTH: 603 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

ATGGGGAACA GCAAAAGTGG GGCCCTGTCC AAGGAGATCC TGGAGGAGCT GCAGCTGAAC 60

ACCAAGTTCT CGGAGGAGGA GCTGTGCTCC TGGTACCAGT CCTTCCTGAA GGACTGTCCC 120

ACCGGCCGCA TCACCCAGCA GCAGTTCCAG AGCATCTACG CCAAGTTCTT CCCGACACCG 180

ACCCCCAAGG CCTACGCCCA GCATGTGTTC CGCAGCTTCG ATTCCAACCT CGACGGCACC 240

CTGGACTTCA AGGAGTACGT CATCGCCCTG CACATGACCA CCGCGGGCAA GACCAACCAG 300

AAGCTGGAGT GGGCCTTCTC CCTCTACGAC GTGGACGGTA ACGGGACCAT CAGCAAGAAT 360

GAAGTGCTGG AGATCGTCAT GGCTATTTTC AAAATGATCA CTCCCGAGGA CGTGAAGCTC 420

CTTCCAGACG ATGAAAACAC GCCGGAAAAG CGAGCCGAGA AGATCTGGAA GTACTTTGGA 480

AAGAATGATG ATGATAAACT TACAGAGAAA GAATTCATTG AGGGGACACT GGCCAATAAG 540

GAAATTCTGC GACTGATCCA GTTTGAGCCT CAAAAAGTGA AGGAAAAGAT GAAGAACGCC 600

TGA 603

( 2 ) INFORMATION FOR SEQ ID NO:3:

( i ) SEQUENCE CHARACTERISTICS:
( A ) LENGTH: 1100 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

GAATTCCGGG CCCAGCCTGC GGCCAGGGGA CCACGCACGT CCCACCCACC CAGCGACTCC 60

CCAGCCGCTG CCCACTCTTC CTCACTCATG GGGAACAGCA AAAGTGGGGC CCTGTCCAAG 120

GAGATCCTGG AGGAGCTGCA GCTGAACACC AAGTTCTCGG AGGAGGAGCT GTGCTCCTGG 180

-continued

| | | | | | | |
|---|---|---|---|---|---|---|
| TACCAGTCCT | TCCTGAAGGA | CTGTCCCACC | GGCCGCATCA | CCCAGCAGCA | GTTCCAGAGC | 240 |
| ATCTACGCCA | AGTTCTTCCC | GACACCGACC | CCCAAGGCCT | ACGCCCAGCA | TGTGTTCCGC | 300 |
| AGCTTCGATT | CCAACCTCGA | CGGCACCCTG | GACTTCAAGG | AGTACGTCAT | CGCCCTGCAC | 360 |
| ATGACCACCG | CGGGCAAGAC | CAACCAGAAG | CTGGAGTGGG | CCTTCTCCCT | CTACGACGTG | 420 |
| GACGGTAACG | GGACCATCAG | CAAGAATGAA | GTGCTGGAGA | TCGTCATGGC | TATTTTCAAA | 480 |
| ATGATCACTC | CCGAGGACGT | GAAGCTCCTT | CCAGACGATG | AAAACACGCC | GGAAAAGCGA | 540 |
| GCCGAGAAGA | TCTGGAAGTA | CTTTGGAAAG | AATGATGATG | ATAAACTTAC | AGAGAAAGAA | 600 |
| TTCATTGAGG | GGACACTGGC | CAATAAGGAA | ATTCTGCGAC | TGATCCAGTT | TGAGCCTCAA | 660 |
| AAAGTGAAGG | AAAAGATGAA | GAACGCCTGA | TGCCAACTGT | TCAGCTCTCC | TCCCTCCACC | 720 |
| TACCACTCAC | ATGACACCCG | TGAGCGCCTG | TGCACACACA | CACACATGCA | CACACACGCG | 780 |
| CGCGCACACA | CACACACACA | CATCCACCCC | AGGGCCAAGA | GAAAGGCCTG | CACACAAGCC | 840 |
| CACAGCACAG | CTCCCTGCCA | AACTGAAGCA | TCTGTAGTGA | CCCACTGGTT | CCTTCTTCCT | 900 |
| GGGTCTTCAG | CATTCCCTCC | CATCATGCCC | GGTCCCACCC | CTCCCTCTGT | CCACCAGCCA | 960 |
| TGGCCCTGTG | CTAATCCCAG | GATTAGGCCA | TAGGAGTCCT | AAGTGTCACC | CCGCTGTAAG | 1020 |
| CTCCTTTGTG | GAGTGCTGGG | TAAGCAGTTT | CCAATAAACG | CAAGCTGAGC | TGGAAAAAAA | 1080 |
| AAAAAAAAAA | ACCGGAATTC | | | | | 1100 |

( 2 ) INFORMATION FOR SEQ ID NO:4:

( i ) SEQUENCE CHARACTERISTICS:
( A ) LENGTH: 200 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: human CAR Antigen ( x i ) SEQUENCE DESCRIPTION: SEQ ID NO:4:

Met Gly Asn Ser Lys Ser Gly Ala Leu Ser Lys Glu Ile Leu Glu Glu
1 5 10 15

Leu Gln Leu Asn Thr Lys Phe Ser Glu Glu Glu Leu Cys Ser Trp Tyr
20 25 30

Gln Ser Phe Leu Lys Asp Cys Pro Thr Gly Arg Ile Thr Gln Gln Gln
35 40 45

Phe Gln Ser Ile Tyr Ala Lys Phe Phe Pro Asp Thr Asp Pro Lys Ala
50 55 60

Tyr Ala Gln His Val Phe Arg Ser Phe Asp Ser Asn Leu Asp Gly Thr
65 70 75 80

Leu Asp Phe Lys Glu Tyr Val Ile Ala Leu His Met Thr Thr Ala Gly
85 90 95

Lys Thr Asn Gln Lys Leu Glu Trp Ala Phe Ser Leu Tyr Asp Val Asp
100 105 110

Gly Asn Gly Thr Ile Ser Lys Asn Glu Val Leu Glu Ile Val Met Ala
115 120 125

Ile Phe Lys Met Ile Thr Pro Glu Asp Val Lys Leu Leu Pro Asp Asp
130 135 140

-continued

Glu Asn Thr Pro Glu Lys Arg Ala Glu Lys Ile Trp Lys Tyr Phe Gly
145 150 155 160

Lys Asn Asp Asp Asp Lys Leu Thr Glu Lys Glu Phe Ile Glu Gly Thr
165 170 175

Leu Ala Asn Lys Glu Ile Leu Arg Leu Ile Gln Phe Glu Pro Gln Lys
180 185 190

Val Lys Glu Lys Met Lys Asn Ala
195 200

( 2 ) INFORMATION FOR SEQ ID NO:5:

( i ) SEQUENCE CHARACTERISTICS:
( A ) LENGTH: 201 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Bovine Recoverin ( x i ) SEQUENCE DESCRIPTION: SEQ ID NO:5:

Met Gly Asn Ser Lys Ser Gly Ala Leu Ser Lys Glu Ile Leu Glu Glu
1 5 10 15

Leu Gln Leu Asn Thr Lys Phe Thr Glu Glu Glu Leu Ser Ser Trp Tyr
20 25 30

Gln Ser Phe Leu Lys Asp Cys Pro Ser Gly Arg Ile Thr Arg Gln Glu
35 40 45

Phe Gln Thr Ile Tyr Ser Lys Phe Phe Pro Gly Ala Asp Pro Lys Ala
50 55 60

Tyr Ala Gln His Val Phe Arg Ser Phe Asp Ala Asn Ser Asp Gly Thr
65 70 75 80

Leu Asp Phe Lys Glu Tyr Val Ile Ala Leu His Met Thr Ser Ala Gly
85 90 95

Lys Thr Asn Gln Lys Leu Glu Trp Ala Phe Ser Leu Tyr Asp Val Asp
100 105 110

Gly Asn Gly Thr Ile Ser Lys Asn Glu Val Leu Glu Ile Val Met Ala
115 120 125

Ile Phe Lys Met Ile Ser Pro Glu Asp Thr Lys His Leu Pro Glu Asp
130 135 140

Glu Asn Thr Pro Glu Lys Arg Ala Glu Lys Ile Trp Gly Phe Phe Gly
145 150 155 160

Lys Lys Asp Asp Asp Lys Leu Thr Glu Lys Glu Phe Ile Glu Gly Thr
165 170 175

Leu Ala Asn Lys Glu Ile Leu Arg Leu Ile Gln Phe Glu Pro Gln Lys
180 185 190

Val Lys Glu Lys Leu Lys Asp Lys Lys
195 200

23 KD HUMAN RETINAL CAR ANTIGEN

This application is a continuation of application Ser. No. 08/343,827, filed Nov. 22, 1994, now abandoned, which is a continuation of application Ser. No. 07/874,843, filed Apr. 28, 1992, now abandoned.

BACKGROUND OF THE INVENTION

1. Field of the Invention

This invention relates to purified polypeptides that can selectively inhibit the binding of the 23 Kd human CAR antigen or human recoverin to mammalian CAR serum and to other related molecules and methods. The polypeptides of the invention are useful as early screening tools for diseases such as small cell carcinoma of the lung (SCCL) and cancer associated with vision loss. Polyribonucleotides encoding the polypeptides of this invention are useful for the mass production of these molecules in substantially pure form.

2. Description of the Background

Paraneoplastic phenomena are secondary neurological effects of various cancer in humans. These phenomena comprise a wide variety of central nervous system (CNS) disorders affecting the brain, muscle movement, and eye vision. One of these paraneoplastic phenomena is degenerative cancer-associated retinopathy (CAR). This is a rare secondary effect that involves the rapid loss-of vision. CAR has been associated with a variety of cancers or neoplasias. It is, however, most frequently encountered in small cell (oat cell) carcinoma of the lung (SCCL), a neoplasm commonly associated with tobacco smoking.

Small cell carcinomas are believed to originate from Kulchitsky cells located in the tracheobronchial mucosa. These cells exhibit neuroendocrine properties that link them to the CNS. Small cell carcinomas are exceptional in that they synthesize and release a variety of small molecular weight biologically active peptides. Some of these peptides have been found to have profound neurological effects.

One specific retinal protein, the 23 Kd retinal CAR antigen, was identified as a key component in the immunological events that accompany these paraneoplastic retinopathies.

Although the biological mechanisms involved in paraneoplastic degenerative retinopathies are not clearly understood, they are known to be immunologically driven. The peculiar antibody reactions encountered in patients afflicted with them suggest autoimmunity at least as a contributing factor. Thirkill, Ch., E.,et al, Arch. Ophthalmol., in press (1992), obtained rabbit polyclonal antibodies to a somewhat impure preparation of the CAR antigen.

Auto-antibodies were identified in the CNS of patients with cancer, primarily with SCCL associated neuropathies. Furthermore, high titers of serum autoantibodies that react with retinal components were seen in patients with cancer experiencing a sudden, unexplained reduction in vision. The antibodies appeared before the cancer was diagnosed. Auto-antibodies to retinal ganglion cells were also observed in patients with CAR. Lung cancer cells of these patients were cultivated in vitro.

Thirkill et al, New Eng. J. Med. 321:1589 (1989), described a case of CAR syndrome in a patient with serum auto-antibodies. The patient's auto-antibodies reacted with retinal, optic nerve and cancer cells. The passive transfer of that patient's serum into guinea pig optic nerve resulted in extensive demyelinization.

The present inventor, in association with others, studied cancer patients experiencing rapid and unexplained vision loss. All the patients showed high serum titers of antibodies reactive with the 23 Kd retinal CAR antigen.

Bovine recoverin is a calcium binding protein located within the photoreceptor cells of the retina. This protein was shown to be involved in the activation and regulation of guanylate cyclase, an enzyme active in the regulation of rhodopsin function. Thus, recoverin plays an essential role in the phototransduction cascade initiated by rhodopsin. Recoverin's in vitro inhibition of the guanylate cyclase enzyme was shown to interfere with photoreceptor function and to lead to cytolysis and a loss of photoreceptors. Under laboratory conditions, antibodies specific for recoverin were shown to neutralize its activation of guanylate cyclase. (Dizhoor et al, Science 251:915 (1991)).

Accordingly, it would be desirable to provide an agent that is capable of detecting early signs of the auto-immune response associated with vision loss in humans afflicted with certain neoplasia's. Such agent would provide a significant tool for screening and early detection of humans at risk.

SUMMARY OF THE INVENTION

This invention relates to a substantially homogeneous, isolated polypeptide capable of selectively inhibiting the binding of 23 Kd human retinal CAR antigen to mammalian CAR serum.

This invention also relates to the substantially homogeneous, isolated 23 Kd human retinal CAR antigen having the amino acid sequence Met Gly Asn Ser Lys Ser Gly Ala Leu Ser Lys Glu Ile Leu Glu Glu Leu Gln Leu Asn Thr Lys Phe Ser Glu Glu Glu Leu Cys Ser Trp Tyr Gln Ser Phe Leu Lys Asp Cys Pro Thr Gly Arg Ile Thr Gln Gln Gln Phe Gln Ser Ile Tyr Ala Lys Phe Phe Pro Thr Pro Thr Pro Lys Ala Tyr Ala Gln His Val Phe Arg Ser Phe Asp Ser Asn Leu Asp Gly Thr Leu Asp Phe Lys Glu Tyr Val Ile Ala Leu His Met Thr Thr Ala Gly Lys Thr Asn Gln Lys Leu Glu Trp Ala Phe Ser Leu Tyr Asp Val Asp Gly Asn Gly Thr Ile Ser Lys Asn Glu Val Leu Glu Ile Val Met Ala Ile Phe Lys Met Ile Thr Pro Glu Asp Val Lys Leu Leu Pro Asp Asp Glu Asn Thr Pro Glu Lys Arg Ala Glu Lys Ile Trp Lys Tyr Phe Gly Lys Asn Asp Asp Asp Lys Leu Thr Glu Lys Glu Phe Ile Glu Gly Thr Leu Ala Asn Lys Glu Ile Leu Arg Leu Ile Gln Phe Glu Pro Gln Lys Val Lys Glu Lys Met Lys Asn Ala (SEQ. ID No: 1);

analogs thereof substituted at amino acids 88, 89, 90, 91, 92, 93 or 94 with Gly, Asn,Ser or Lys; Ser, Gly, Ala or Cys; Thr, Ser, Gly or Met; Asn, Ser, Arg or Gly; Asn, Ser, His or Met; Gly, Asn, Arg or Ile; Ala, Leu, Lys or Ala; Glu, Ser, Arg or Lys; and fragments and precursors thereof about 7 to 10 amino acids long, and 10 to 100 amino acids long, comprising at least amino acids 88 to 100, 100 to 150, 100 to 200 or 88 to 197;

Also part of this invention is a composition, comprising the polypeptide of this invention; and a non-proteolytic carrier.

Still part of this invention is a substantially homogeneous, isolated fusion protein that comprises a label polypeptide and the polypeptide of the invention described above.

This invention also encompasses a method of producing the polypeptide of the invention in a substantially homogeneous, isolated form, by obtaining a hybrid vector carrying a DNA sequence encoding the polypeptide;

transforming a host cell with the hybrid vector; and culturing the transformed cell under conditions effective to express the peptide.

Also described herein is a method of producing the polypeptide of this invention in substantially pure form, comprising obtaining a hybrid vector carrying a DNA sequence encoding the polypeptide;

transforming a host cell with the hybrid vector;

culturing the host cell transformed with the hybrid vector carrying the polydeoxynucleotide of this invention under conditions effective to express the polypeptide; and allowing the polypeptide to be expressed.

This invention also relates to a deoxypolyribonucleotide that comprises a substantially homogeneous, isolated DNA segment encoding the polypeptides of the invention. Given the redundancy of the genetic code, the invention provides three polyribonucleotide sequences for each polypeptide, analog, fragment and precursor thereof.

By means of example, the polynucleotide may have a sequence selected from the group consisting of ATG GGG AAC AGC AAA AGT GGG GCC CTG TCC AAG GAG ATC CTG GAG GAG CTG CAG CTG AAC ACC AAG TTC TCG GAG GAG GAG CTG TGC TCC TGG TAC CAG TCC TTC CTG AAG GAC TGT CCC ACC GGC CGC ATC ACC CAG CAG CAG TTC CAG AGC ATC TAC GCC AAG TTC TTC CCG ACA CCG ACC CCC AAG GCC TAC GCC CAG CAT GTG TTC CGC AGC TTC GAT TCC AAC CTC GAC GGC ACC CTG GAC TTC AAG GAG TAC GTC ATC GCC CTG CAC ATG ACC ACC GCG GGC AAG ACC AAC CAG AAG CTG GAG TGG GCC TTC TCC CTC TAC GAC GTG GAC GGT AAC GGG ACC ATC AGC AAG AAT GAA GTG CTG GAG ATC GTC ATG GCT ATT TTC AAA ATG ATC ACT CCC GAG GAC GTG AAG CTC CTT CCA GAC GAT GAA AAC ACG CCG GAA AAG CGA GCC GAG AAG ATC TGG AAG TAC TTT GGA AAG AAT GAT GAT GAT AAA CTT ACA GAG AAA GAA TTC ATT GAG GGG ACA CTG GCC AAT AAG GAA ATT CTG CGA CTG ATC CAG TTT GAG CCT CAA AAA GTG AAG GAA AAG ATG AAG AAC GCC TGA (SEQ. ID No: 2); and redundant DNA sequences thereof encoding the 23 Kd human retinal CAR antigen.

Also provided herein is a substantially homogeneous, isolated deoxyribonucleotide that comprises the deoxypolyribonucleotide described above and a DNA encoding a label polypeptide or a label fragment thereof, the DNA being operatively linked to the deoxypolyribonucleotide and being inducible.

This invention also encompasses a hybrid vector carrying the substantially homogeneous deoxypolyribonucleotide of the invention, and a host cell transformed with the hybrid vector, the hybrid cell being capable of expressing the polypeptide of this invention.

Still part of this invention is a polyribonucleotide that comprises a substantially homogeneous, isolated RNA segment encoding the polypeptide of the invention.

Also disclosed herein is an oligoribonucleotide comprising the substantially pure, isolated deoxypolyribonucleotide of this invention, and an RNA operatively linked thereto encoding a label polypeptide or a label fragment thereof.

This invention also encompasses a monoclonal antibody or fragment thereof capable of specifically inhibiting the binding of mammalian CAR serum to the 23 Kd human retinal CAR antigen.

Still part of the invention is a hybridoma cell capable of secreting a monoclonal antibody having specificity for the 23 Kd human retinal CAR antigen.

Also provided herein is an in vitro method of diagnosing CAR, comprising contacting the polypeptide of the invention with the serum of an at risk subject; and detecting the occurrence of any specific binding of the serum to the polypeptide.

This invention also encompasses an in vitro method of diagnosing CAR, comprising contacting the fusion protein of the invention with the serum of an at risk subject; and detecting the occurrence of any specific binding of the serum to the fusion protein.

An in vitro method for diagnosing small cell carcinoma of the lung(SCCL) is provided herein, that comprises contacting the polypeptide of the invention with the serum of an at risk subject; and detecting the occurrence of any specific binding of the serum to the polypeptide.

This invention also relates to an in vitro method of diagnosing SCCL, comprising contacting the fusion protein of the invention with the serum of an at risk subject; and detecting the occurrence of any specific binding of the serum to the fusion protein.

Also described herein is an in vitro method for diagnosing neoplasias associated with vision loss, comprising contacting the polypeptide of the invention with the serum of a patient afflicted with vision loss; and detecting the occurrence of any specific binding of the serum to the polypeptide.

This invention also discloses an in vitro method for diagnosing neoplasias associated with vision loss, comprising contacting the fusion protein of the invention with the serum of a patient afflicted with vision loss; and detecting the occurrence of any specific binding of the serum antibodies to the fusion protein.

Another part of this invention relates to a kit for screening of a neoplasias associated with vision loss, that comprises the polypeptide described above; and instructions for its use.

This invention also relates to a kit for diagnosing neoplasias associated with vision loss, comprising the fusion protein of this invention; and instructions for its use.

A more complete appreciation of the invention and many of the attendant advantages thereof will be readily perceived as the same becomes better understood by reference to the following detailed description. Other objects, advantages and features of the present invention will also become apparent to those skilled in the art from the following discussion.

BEST MODE FOR CARRYING OUT THE INVENTION

This invention arose from a desire by the inventor to elucidate the autoimmune response seen in patients afflicted with CAR syndrome and ascertain the role of the 23 Kd human retinal CAR antigen in this response.

The inventor used serum antibodies from a CAR patient to isolate the corresponding gene from a human retinal DNA library. The polynucleotide sequence of the gene encoding the CAR antigen showed a high correlation with the DNA sequence encoding the bovine photoreceptor protein recoverin described by Dizhoor et al (1991), Supra.

The present human polypeptide differs in about 23 out of 201 amino acids when compared with bovine recoverin. This is a greater than 10% difference. However, since bovine recoverin is known to activate guanylate cyclase, its immunological inactivation may result in the loss of photoreceptors, that is characteristic of cancer-associated retinopathies.

An analysis of the DNA sequence encoding the human retinal CAR antigen cloned by the inventor indicates that the CAR antigen is recoverin, the calcium binding protein located within the photoreceptor cells of the retina. If the neutralization of recoverin by auto-antibodies seen in laboratory studies occurs in vivo in CAR patients, any prolonged immunological inhibition of guanylate cyclase will necessarily interfere with photoreceptor function and lead to cytolysis and loss of photoreceptors. All these effects have been observed in patients afflicted with CAR.

It is known that the blood-retinal barrier prevents the direct access of serum antibodies to ocular tissues in vivo. The serum antibodies to the 23 Kd retinal CAR antigen most likely develop as a consequence of the actions of other components of the immune system. For instance, the initial trigger mechanism for the production of the auto-antibodies may be the host's response to the appearance of a neoplasm. The paraneoplastic retinopathy phenomenon, in all likelihood, reflects a response to the neoplasia itself. Thus, the appearance of a neoplasia may sensitize the host to the 23 Kd retinal CAR antigen through the aberrant production of an immunologically similar antigen. In response to this the host's immune system responds by producing anti-CAR antibodies (autoimmune response). The serum antibodies having specificity for the retinal CAR antigen cannot, however, be the primary cause of vision loss because they cannot cross the blood-brain barrier to screen the retina. Their presence in the serum of CAR patients, nevertheless, exhibits a high degree of correlation with CAR associated neoplasias. No such specificity of these antibodies has been seen for other forms of retinopathies. This correlation lead the present inventor to the development of a kit for, and method of early detection of certain neoplasias associated with vision loss by screening patients' blood for anti-CAR antibodies.

The initiation of an autoimmune response in the retina, such as is the case in paraneoplastic retinopathy as a response to a neoplasia, depends on the ability of any immune components to cross the blood-retinal barrier to act on ocular tissues. As already discussed, antibodies cannot cross the blood-brain barrier and are therefore not suspected of direct involvement in the retinal damage observed. Somewhat more diffusible components of the immune system, such as cytokines, e.g., interleukins, have been demonstrated in animal models to be highly organ selective and cell-specific in their cytotoxicity. In CAR, these cytokines are mobilized and may possibly cause the leakage of specific intraocular photoreceptor antigens to the blood stream and, therefore, expose them to the body's immune surveillance. These events may thus result directly or indirectly in autoimmune retinopathy.

CAR patients, however, do not exhibit comparable hypersensitivity to other internalized photoreceptor antigens, such as rhodopsin or the retinal S-antigen, although these are recognized as being highly antigenic. Similarly, in animal models of experimental allergic uveitis, it has been shown that the predominating immunological response is overwhelmingly directed against the inciting antigen with relatively less response directed towards other photoreceptor components.

CAR and other neuropathies, such as paraneoplastic cerebellar degenerations associated with cancers, are usually detectable substantially ahead of the diagnosis of the respective cancers. The strong association of CAR antibody reactions with vision loss, thus, provides a strong tool for the application of the present technology to the immunologic screening and early detection of specific forms of cancer. Clearly, early detected cancers can be treated far more successfully than those detected at a later time.

The present invention, thus, provides a substantially homogeneous polypeptide capable of selectively inhibiting the binding of the 23 Kd human CAR antigen or recoverin to mammalian CAR serum.

This invention provides a variety of polypeptides of different lengths and sequences, all of which are closely related to the 23 Kd human CAR antigen. Typically, the polypeptides of the invention are capable of inhibiting the binding of auto-antibodies in the serum of a CAR patient with the CAR-associated retinal photoreceptor.

The inhibition essay may be, e.g., any ELISA assay conducted as described by Hornbeck, P., in Current Protocols in Immunology, Section 2.1.2, J. E. Colegam, A. M. Kruisbeek (eds.), Green Publ. Asc., Wiley-Interscience, N. Y., (1991) or Linscott's Directory of Immunol. and Biol. Regents, Santa Rosa, Calif. (1991/92). A radioimmunoassay may also be utilized, as is known in the art. Typically, the serum is diluted to about 1:10 to 1:1,000 in PBS-Tween buffer and the polypeptide and the labeled 23 Kd antigen are added to a final concentration of about 0.01 mg/ml and about 0.01 to 0.001 mg/ml respectively. The mixture is then allowed to stand at about 4° C. to room temperature for about 60 to 120 minutes. If the 23 Kd antigen is bound to a solid support prior to starting the assay, the counts bound to the solid support at the end of the assay may be compared to those bound thereto in a control experiment conducted in the absence of the polypeptide and calculate the degree of inhibition attained.

However, any other competition essays that are suitable for assessing selectively in the binding of a polypeptide to an antibody by competition with serum antibodies an antigen may also be utilized herein. Other immunoassays may also be utilized, as are known in the art.

In one preferred embodiment of the invention, the polypeptide comprises an amino acid sequence selected from the group consisting of the 23 Kd human retinal CAR antigen, analogs thereof and fragments and precursors thereof that selectively bind to human CAR serum.

The inventor found the 23 Kd human retinal CAR antigen to comprise the amino acid sequence shown in Table 1 below.

TABLE 1

| 23 Kd Human Retinal CAR Antigen Sequence | | | | | | | | | | | | | | | |
|---|---|---|---|---|---|---|---|---|---|---|---|---|---|---|---|
| Met | Gly | Asn | Ser | Lys | Ser | Gly | Ala | Leu | Ser | Lys | Glu | Ile | Leu | Glu | Glu |
| 1 | | | | 5 | | | | | 10 | | | | | 15 | |
| Leu | Gln | Leu | Asn | Thr | Lys | Phe | Ser | Glu | Glu | Glu | Leu | Cys | Ser | Trp | Tyr |
| | | | 20 | | | | | 25 | | | | | 30 | | |
| Gln | Ser | Phe | Leu | Lys | Asp | Cys | Pro | Thr | Gly | Arg | Ile | Thr | Gln | Gln | Gln |
| | | 35 | | | | | 40 | | | | | 45 | | | |
| Phe | Gln | Ser | Ile | Tyr | Ala | Lys | Phe | Phe | Pro | Asp | Thr | Asp | Pro | Lys | Ala |
| | 50 | | | | | 55 | | | | | 60 | | | | |
| Tyr | Ala | Gln | His | Val | Phe | Arg | Ser | Phe | Asp | Ser | Asn | Leu | Asp | Gly | Thr |
| 65 | | | | | 70 | | | | | 75 | | | | | 80 |
| Leu | Asp | Phe | Lys | Glu | Tyr | Val | Ile | Ala | Leu | His | Met | Thr | Thr | Ala | Gly |
| | | | | 85 | | | | | 90 | | | | | 95 | |
| Lys | Thr | Asn | Gln | Lys | Leu | Glu | Trp | Ala | Phe | Ser | Leu | Tyr | Asp | Val | Asp |
| | | | 100 | | | | | 105 | | | | | 110 | | |
| Gly | Asn | Gly | Thr | Ile | Ser | Lys | Asn | Glu | Val | Leu | Glu | Ile | Val | Met | Ala |
| | | 115 | | | | | 120 | | | | | 125 | | | |
| Ile | Phe | Lys | Met | Ile | Thr | Pro | Glu | Asp | Val | Lys | Leu | Leu | Pro | Asp | Asp |
| | 130 | | | | | 135 | | | | | 140 | | | | |
| Glu | Asn | Thr | Pro | Glu | Lys | Arg | Ala | Glu | Lys | Ile | Trp | Lys | Tyr | Phe | Gly |
| 145 | | | | | 150 | | | | | 155 | | | | | 160 |
| Lys | Asn | Asp | Asp | Asp | Lys | Leu | Thr | Glu | Lys | Glu | Phe | Ile | Glu | Gly | Thr |
| | | | | 165 | | | | | 170 | | | | | 175 | |
| Leu | Ala | Asn | Lys | Glu | Ile | Leu | Arg | Leu | Ile | Gln | Phe | Glu | Pro | Gln | Lys |
| | | | 180 | | | | | 185 | | | | | 190 | | |
| Val | Lys | Glu | Lys | Met | Lys | Asn | Ala | | | | | | | | |
| | | 195 | | | | | 200 | | | | | | | | |
| (Seq. No. 1) | | | | | | | | | | | | | | | |

The brackets in Table 1 above show the two binding sites for calcium in the polypeptide sequence.

The analogs of the polypeptide of the invention may comprise the amino acid sequence of the 23 Kd human retinal CAR antigen substituted at least once with Arg, His, Lys or Asp at amino acid(s) 5, 11, 12, 15, 16, 25 or 26, 27, 28; with Glu or Met at amino acid(s) 22 or 23; with His or Lys at amino acid(s) 43 or 55; with Arg at amino acid(s) 63, 68 or 71; with His, Lys, Glu or Arg; and Asp at amino acid(s) 74, 78, 82 or 84.

Other examples of analogs are those where any of the non-polar amino acids are substituted with other non-polar amino acids. In addition, any basic amino acid may be substituted by another basic amino acid. Similarly, any acidic amino acid may be substituted by another acidic amino acid. All the substitutions generally are in the positions indicated above. However, other positions may also be suitable for substitutions.

Particularly preferred analogs are those where the substitutions occur in one or the other calcium binding sequences, or in both. The location of these amino acids is shown in Table 1 above. This provides a large number of analogs, all of which are suitable for use herein, as are fragments thereof as described below.

All analogs suitable for use herein are capable of binding to CAR serum antibodies and inhibit the CAR serum binding to the 23 Kd antigen in an assay conducted by any of the methods referred to above. Such competitive assays are conducted under conditions that an artisan would know.

The fragments of the 23 Kd human retinal CAR antigen and its analogs may be about 20 to 100 amino acids long, and more preferably about 50 to 100 amino acids long. Typically, preferred fragments comprise amino acids 1 to 92, 92 to 126, and 126 to 197.

Examples of fragments suitable for use herein are the following. Preferred fragments are those comprising from about Met 1 to about Met 92, from about Met 1 to about Met 126, from about Met 1 to about Met 197, from about Met 92 to about Met 126, from about Met 92 to about Met 197 and from about Met 126 to about Met 197. All fragments, whether of the CAR antigen or its analogs are capable of binding human CAR serum antibodies and inhibiting the binding of CAR serum to the 23 Kd human antigen.

Precursors are defined within the confines of this invention as polypeptides of molecular weight higher than the antigen, analogs and fragments thereof that comprise their amino acid sequences. In addition, the precursors may also comprise other amino acid sequences unrelated to the antigen, that will not interfere with the precursor's binding to CAR serum antibodies or with the inhibition assay described above.

Examples of precursors suitable for use with the methods of this invention are as follows. An about 3250 Dalton precursor comprising the amino acid sequence

| | | | | | | | | | |
|---|---|---|---|---|---|---|---|---|---|
| Ala | Gln | His | Val | Phe | Arg | Ser | Phe | Asp | Ser Asn |
| | | | | 5 | | | | | 10 |
| Leu | Asp | Gly | Thr | Leu | Asp | Phe | Lys | Gln | Tyr Val |
| | | | 15 | | | | | 20 | |
| Ile | Ala | Leu | His | Met | | | | | |
| | | 25 | | 28 | | | | | |

Another precursor comprises an about 3,000 Dalton precursor comprising

| | | | | | | | | |
|---|---|---|---|---|---|---|---|---|
| Leu | Glu | Tyr | Ala | Phe | Ser | Leu | Tyr | Asp |
| | | | | 5 | | | | |
| Val | Asp | Gly | Thr | Ile | Ser | Lys | Asn | Glu |
| 10 | | | | | 15 | | | |
| Val | Leu | Glu | Ile | Val | Met | Ala | Ile | |
| | 20 | | | | | 25 | | |

However, other precursors are also suitable, including those with longer or shorter amino acid sequences that comprise the noted segments.

All precursors are capable of inhibiting the binding of mammalian CAR serum to the 23 Kd human antigen as described above. However, other analogues and/or fragments and/or precursors are also suitable for the present applications.

The polypeptides of this invention may be synthesized by methods known in the art (e.g., Peptide Chemistry, A Practical Textbook, M. Bodansky, Ed., Springer-Verlag, NY, NY (1988)). Other methods may also be utilized, including producing the polypeptides by culturing the recombinant host of this invention.

This invention also provides a composition, comprising the substantially homogeneous, isolated polypeptide of the invention; and a non-proteolytic carrier.

The carrier may be any carrier, e.g., aqueous solutions for diagnostic purposes, as long as it does not degrade the polypeptide.

When for therapeutic purposes, the composition comprises a pharmaceutically-acceptable carrier. These are known in the art and need not be further described herein.

As above, any aqueous carrier that will not degrade the fusion protein is suitable. When the composition is a therapeutic composition the carrier is also pharmaceutically acceptable. The composition preferably comprises about 0.1 to 99.9 wt % of the fusion protein, and more preferably about 1 to 20 wt % thereof.

This invention also provides a substantially homogeneous, isolated deoxypolyribonucleotide, that comprises a substantially homogeneous, isolated DNA segment that encodes the polypeptide of the invention. Given the degeneracy of the genetic code, at least three DNA sequences are possible for each amino acid sequence. All of these are encompassed herein.

By means of example, one DNA segment sequenced by the inventors comprises the deoxycribonucleotides shown in Table 2 below.

TABLE 2

Polynucleotide Sequence Encoding
23 Kd Human Retinal CAR Antigen

| | | | | | | | | | | | | | |
|---|---|---|---|---|---|---|---|---|---|---|---|---|---|
| ATG | GGG | AAC | AGC | AAA | AGT | GGG | GCC | CTG | TCC | AAG | GAG | ATC | CTG | 42 |
| GAG | GAG | CTG | CAG | CTG | AAC | ACC | AAG | TTC | TCG | GAG | GAG | GAG | CTG | 84 |
| TGC | TCC | TGG | TAC | CAG | TCC | TTC | CTG | AAG | GAC | TGT | CCC | ACC | GGC | 126 |
| CGC | ATC | ACC | CAG | CAG | CAG | TTC | CAG | AGC | [ATC | TAC | GCC | AAG | TTC | 168 |
| TTC | CCG | ACA | CCG | ACC | CCC | AAG | GCC | TAC | GCC | CAG | CAT | GTG | TTC | 210 |
| CGC | AGC | TTC | GAT | TCC | AAC | CTC | GAC | GGC] | ACC | CTG | GAC | TTC | AAG | 252 |
| GAG | TAC | GTC | [ATC | GCC | CTG | CAC | ATG | ACC | ACC | GCG | GGC | AAG | ACC | 294 |
| AAC | CAG | AAG | CTG | GAG | TGG | GCC | TTC | TCC | CTC | TAC | GAC | GTG | GAC | 336 |
| GGT | AAC | GGG] | ACC | ATC | AGC | AAG | AAT | GAA | GTG | CTG | GAG | ATC | GTC | 378 |
| ATG | GCT | ATT | TTC | AAA | ATG | ATC | ACT | CCC | GAG | GAC | GTG | AAG | CTC | 420 |
| CTT | CCA | GAC | GAT | GAA | AAC | ACG | CCG | GAA | AAG | CGA | GCC | GAG | AAG | 462 |
| ATC | TGG | AAG | TAC | TTT | GGA | AAG | AAT | GAT | GAT | GAT | AAA | CTT | ACA | 504 |
| GAG | AAA | GAA | TTC | ATT | GAG | GGG | ACA | CTG | GCC | AAT | AAG | GAA | ATT | 546 |
| CTG | CGA | CTG | ATC | CAG | TTT | GAG | CCT | CAA | AAA | GTG | AAG | GAA | AAG | 588 |
| ATG | AAG | AAC | GCC | TGA | (SEQ. NO. 2) | | | | | | | | | 603 |

Typically, the composition may comprise about 0.01 to 99.99 wt % of the polypeptide, and more preferably about 0.1 to 15 wt %.

This invention also provides a substantially homogeneous, isolated fusion protein, comprising the polypeptide of the invention and a label protein operationally linked thereto.

The fusion protein may be obtained by cloning the corresponding DNA segments encoding the parts thereof in reading frame to one another and expressing the product as is known in the art (e. g. F. Megret et al., Virology 187(2) :480. (1992)).

Also provided herein is a composition comprising the substantially homogeneous fusion protein; and a non-proteolytic carrier.

The bracketed sections correspond to the amino acid segments involved in calcium binding.

Polyribonucleotide sequences encoding all analogs, fragments and precursors described above are also part of this invention.

Examples of DNA sequences suitable for use as analogs, fragments, and precursors in this invention are those encoding the amino acid sequences described above.

These DNA sequences may be prepared by methods known in the art (e.g., DNA Cloning: A Practical Approach, Volumes I, II, and III, D. M. Glover, Ed., SRL Press, Oxford, England). However, other methods may also be utilized or combinations thereof, including mutations of existing sequences, substitutions, deletions and the like.

Also provided herein is a hybrid vector carrying the deoxyribonucleotide described above.

Suitable vectors are those vectors known in the art for applications in the cloning of DNA segments. Particularly suitable are expression vectors that may be used for expressing the gene product in bacteria, yeast and mammalian cells. These are known in the art as are the technologies for cloning, DNA separation, transfection and cell growth that, therefore, need not be described herein in further detail (e.g., Gene Transfer and expression Protocols, E. J. Murray, Ed., Humana Press, Clifton, N.J. (1991)). However, other methods may also be utilized.

Examples of suitable vectors are M13 Bluescript, λgt 11, Baculovirus, and pXT1, among others. Also provided herein is a substantially pure host cell transformed with a vector of this invention. If the cell is a mammalian cell then the vector must be capable of transfecting the mammalian cell, growing and allowing the expression of the gene product therein. Similarly, if the cell is a bacterium or yeast, the vector must be one suitable for transfection, growth and expression of the gene product in the corresponding type of cell.

Also provided herein is a substantially homogeneous, isolated oligoribonucleotide, comprising the substantially homogeneous, isolated deoxypolyribonucleotide of this invention; and a DNA sequence operationally linked thereto encoding a label protein, the DNA sequence being capable of inducibly amplifying the expression of the fusion protein.

An example of a label protein is β-galactosidase. However, others may also be utilized for the overproduction of the fusion protein.

The oligoribonucleotide may be synthesized by methods known in the art, such as the dideoxy method mentioned above.

This invention also provides a method of producing the polypeptide of the invention, that comprises obtaining a hybrid vector carrying a DNA encoding the polypeptide;

transforming a host cell with the hybrid vector; and culturing the transformed cell under conditions effective to express the polypeptide.

The hybrid vector of the invention may be obtained by methods known in the art. Briefly, the DNA sequence encoding a desired polypeptide by methods known in the art and then cloned into a vector, such as an expression vector. Other vectors, however, may also be utilized. The sequence as contained in the vector must be capable of permitting replication, transcription and expression, either by the vector itself or in conjunction with a cryptic DNA. A suitable host cell is then transformed with the hybrid vector using technology that is known in the art (e.g., Gene Transfer and Expression Protocols, E. J. Murray Ed., Humana Press, Clifton, N.J. (1991)).

Examples of vectors are M13, Bluescript, and λgt11, among others. Examples of host cells are *E. coli*, JM101, and JM107, among others (e.g., Yanisch-Perron et al, Gene 33:103 (1983)).

The thus transformed cell is then cultured under specific conditions which permit the expression of the desired polypeptide. Typically, if the vector contains DNA sequences permitting the expression of cloned DNA, all that is needed is an expression medium so that the polypeptide may be produced. Alternatively, if the vector DNA does not contain all the sequences necessary for expressing a polypeptide, a cryptic DNA to aid in that function is also provided to the host. This system is then incubated at a range of temperature where the cells may grow and express the polypeptide. Temperature sensitive gene expression commonly requires the vector to be incubated at about 42° C. for about 2 hours prior to productive incubation at 37° C. for 6 hours, during which the polypeptide is expressed. Other conditions, if suitable, are also within this invention.

Depending on the volume and number of cells utilized the culture will reach confluence in about 4 to 6 hrs and, therefore, after a period of about 8 hrs, the reaction may be stopped.

The thus produced polypeptide may then be purified by separation from the reaction medium and the cells as is known in the art. Any suitable methods may be utilized as long as the integrity of the proteinaceous material is preserved.

If the polypeptide is produced via the fusion protein, the oligoribonucleotide may first be synthesized by methods known in the art or by ligation of the DNA sequences encoding the polypeptide of the invention and the label protein with the amplification sequences operationally linked to one another. The DNA may then be cloned into a vector, and the hybrid vector inserted into an appropriate host by methods known in the art. The fusion protein may then be expressed by culturing the recombinant host, purified and cleaved if the pure polypeptide is desired. Enzymes for cleaving at specific sequences are known in the art, as is the technology utilized for the excision of the amino acid sequence at a desired site (e.g., Current Protocols in Molecular Biology, J. E. Colegam, A. M. Kriusbeek (eds.), Green Publ. Asc., Wiley-Interscience, N. Y., (1991)).

Also provided herein are substantially pure homogeneous polyribonucleotides that comprises a mRNA segment encoding the polypeptides of the invention. These are mRNA segments that encode the amino acid sequences of the polypeptides, analogs, fragments and precursors provided herein. The technology for synthesizing the polyribonucleotides, either by addition of ribonucleotides one by one, by transcription from a DNA segment, or a cDNA segment is known in the art and need not be further detailed herein. (e.g., Messing and Viera, Gene 19:259 (1982)).

As in the case of the DNAs, the degeneracy of the genetic code provides three mRNAs for each protein product encoded therein. Examples are mRNAs encoding the about 23 Kd antigen of the invention, analogs with one or more substitutions in their expression products, fragments and precursors thereof corresponding to or encoding the amino acid sequences described above.

All the mRNAs encode polypeptides capable of inhibiting the binding of mammalian CAR serum antibodies to the 23 Kd human retinal CAR antigen.

This patent also encompasses a substantially pure, isolated oligoribonucleotide, comprising deoxyribonucleotide encoding the polypeptide of this invention; and an RNA operationally linked thereto encoding a label polypeptide.

The oligoribonucleotide may be synthesized by transcription of the corresponding DNA, or by other methods.

Also comprised herein is a composition, comprising the oligoribonucleotide of this invention; and a non-RNA degrading carrier.

The composition typically comprises about 0.01 to 99.99 wt % of the oligoribonucleotide and more preferably about 0.5 to 18.5 wt % thereof. Other proportions may also be used.

Also provided herein are substantially pure monoclonal antibodies or fragments thereof that have the capability of specifically inhibiting the binding of mammalian CAR serum to the 23 Kd human retinal CAR antigen. These antibodies have high affinity and specificity for the 23 Kd CAR antigen.

The antibody fragments must preserve the Fab or F'ab portion thereof and, therefore, the antibody's ability to specifically bind to its antigen. The antibody fragment may also be a single chain fragment capable of inhibiting the binding of CAR serum to the 23 Kd antigen. The antibodies may be obtained from a hybridoma cell line, or they may be obtained by recombinant technology by cloning of their corresponding genes (e.g., G. Winter and C. Milstein, Nature 349:293, (1991)). Similarly, the monoclonal fragments may be obtained in the same manner and/or by appropriate excision of the desired sequence by enzyme cleavage. All these techniques are known in the art and need not be described herein.

Also provided herein is a hybridoma cell capable of secreting a monoclonal antibody having high affinity and specificity for the 23 Kd human retinal CAR antigen.

The method of making a hybridoma cell line most relied upon is still that of Kohler and Milstein. The most stable lines are those obtained by cloning an immortal cell, e.g., a myeloma cell with a lymphocyte of mouse or rat. Humanized cell lines may be obtained by including rat or mouse lymphocytes to provide a position of the antibody sequence and, therefore, more stability.

The polypeptides of the invention find one application in an in vitro method of detecting small cell carcinoma of the lung (SCCL), that comprises

- obtaining a body fluid from a subject suspected of being afflicted with SCCL;
- contacting the polypeptide of the invention with an aliquot of the serum of the subject; and
- detecting the occurrence of any specific binding of the serum antibodies to the polypeptide.

In a particularly preferred embodiment, the polypeptide is bound to a solid support, and the detection is conducted by Western blot, ELISA or agglutination assays. The technology associated with these detection methods are widely known in the art and need not be further described herein.

The solid support may be a nitrocellulose or other polymeric sheet in the case of the Western blot technology. In addition, plastic plates or dishes may be used when the interaction between a patient's antibodies and the polypeptide are identified and/or quantified by means of an enzyme-linked immunosorbent assay (ELISA). Similarly, a solid support such as latex or other polymeric beads may be utilized when a patient's antibody binding to the polypeptide of the invention is assessed by agglutination or aggregation of the sensitized latex beads (e.g., Gershoni and Palade, Anal Biochem. 131:1–15 (1983) for Western blots; Voller et al, Manual of Clin. Immunol. Amer. Soc. for Microbiol., Washington, D.C., for ELISA assays; and Pirjo et al, J. Clin. Microbiol. 23 (3): 556 (1986) and Salonen and Vaheri, J. Immunol. Methods 30:209 (1979) for agglutination tests). However, other types of assay known in the art may also be utilized, particularly if they are sensitive and accurate.

Also provided herein is an in vitro method of diagnosing SCCL, comprising

- obtaining a body fluid from a subject suspected of being afflicted with SCCL;
- contacting the fusion protein of the invention with an aliquot of the serum of the subject; and
- detecting the occurrence of any specific binding of the serum antibodies to the fusion protein.

Another application for the polypeptide of this invention is in an in vitro method for diagnosing neoplasias associated with vision loss, that comprises

- contacting the polypeptide of the invention with the serum of a patient afflicted with vision loss; and

- detecting the occurrence of any specific binding of the serum antibodies to the polypeptide.

As in the previous method, the solid support and the detection method may be varied as described above. Elisa's of various kinds as well as radioimmmunoassays are suitable.

General conditions for the practice of the different assays are known in the art (e.g., Hornbeck, P. in: Current Protocols in Immunology, Section 2.1.2, J. E. Colegam, A. M. Kruisbeek (eds.), Green Publ. Asc., Wiley-Interscience, N. Y., (1991)). However, variations thereof are also possible. The antigen may be standardized to contain about 1 mg protein/ml. Serum dilutions may be made that range from about 1:20 to 1:4,000. All are incubated at room temperature. A labeled second antibody may be for instance "Goat anti-human polyvalent immunoglobulin-alkaline phosphatase conjugated, among others. The conditions of the assay are standard in tha art and need not be further detailed herein.

A similar method may be practiced with the fusion protein of this invention,utilizing, e. g.., an antibody specific for the polypeptide or the label protein. In the case of assays utilizing a second antibody, this most likely will be an anti-antibody immunoglobulin or a second anti-polypeptide antibody in the case of a sandwich assay.

In another aspect of this invention, a method for diagnosing a neoplasia associated with vision loss, is provided herein, that comprises

- obtaining a body fluid from a patient suspected of being afflicted with a neoplasia associated with vision loss;
- contacting the fusion protein of this invention with an aliquot of the body fluid under conditions effective to bind the polypeptide to any antibodies specific therefor; and
- detecting the occurrence of any specific binding of a body fluid antibody to the polypeptide.

Particularly preferred embodiments for this method or assay are as described above for the method of diagnosing SCCL. Other types of assays known in the art that are variations thereof may also be utilized, particularly if they are sensitive and accurate.

The above method may also be conducted with the fusion protein of the invention, wherein the binding of any specific antibodies occurs with the polypeptide within the fusion protein or with the label protein. In all the assays provided herein the serum of a subject may be diluted several fold, in many instances up to and over 2,000 times without losing its sensitivity.

As in the prior assays, the fusion protein may be bound to a solid support, and the detection may be conducted by a Western blot, ELISA or agglutination assay.

In still another embodiment, this invention provides an in vitro method of diagnosing CAR that comprises

- obtaining a body fluid from a subject suspected of being afflicted with CAR;
- contacting the polypeptide of this invention with an aliquot of the body fluid under conditions effective to produce binding of the polypeptide to any antibodies specific therefor; and
- detecting the occurrence of any specific binding of a body fluid antibody to the polypeptide. Detection methods have been described above and are also applicable to the present method. The polypeptide, for example may be bound to a solid support, and the detection may be conducted by a Western blot, ELISA or agglutination assay.

Also provided herein is an in vitro method of diagnosing CAR, that comprises obtaining a body fluid from a subject suspected of being afflicted with CAR;

contacting the fusion protein of this invention with an aliquot of the body fluid under conditions effective to produce binding of the polypeptide to any antibodies specific therefor; and detecting the occurrence of any specific binding of a body fluid antibody to the polypeptide. In a particularly preferred embodiment the fusion protein may be bound to a solid support, and the detection of any complex formation may be conducted by a Western blot, ELISA or agglutination assay.

This invention also provides a kit for diagnosing a neoplasia associated with vision loss, comprising at least one of the polypeptides of the invention; and instructions to use the kit.

The kit may further comprise a solid support; and anti-antibodies or immunoglobulins, as well as non-specific serum and/or the 23 Kd antigen and/or 23 Kd antigen-specific antibodies to be used as controls.

The above-described kit is suitable for detection of serum antibodies by Western blot, ELISA or agglutination assays. In the latter case, the solid support may be polymeric beads whereas in the earlier ones it may be a polymeric sheet such as a nitrocellulose sheet or plastic plates or dishes.

For the enzyme-linked immunodetection and capture assay (ELISA), polymeric supports such as plates or dishes may be utilized. All these are known in the art as well as the general details for practicing these assays (e.g., Matsuo et al., Jpn. J. Ophthalmol. 30:472 (1986); Matsuo et al., Jpn. J. Ophthalmol. 30:480 (1986)).

The above method is suitable for the diagnosis of neoplasias as well as CAR, SCCL, and diabetic retinopathy, among others.

Also provided herein is a kit for diagnosing a neoplasia associated with vision loss, that comprises at least one of the fusion proteins of the inventions; and instructions to use the kit.

The kit may further comprise a solid support; and anti-antibodies or immunoglobulins, as well as non-specific serum and/or a fusion protein comprising the 23 Kd antigen and/or 23 Kd antigen-specific antibodies to be used as controls.

Western blot, ELISA or agglutination assays may be employed for the detection of the antibody fusion protein complex. The technology applicable to these assays is known in the art and has been briefly described above in reference to certain citations.

Having now generally described this invention, the same will be better understood by reference to certain specific examples, which are included herein for purposes of illustration only, although not intended to be limiting of the invention or any embodiment thereof, unless so specified.

EXAMPLES

Example 1

Molecular Cloning and Sequencing of 23 Kd Human Retinal CAR Antigen cDNA

A λgt11 cDNA library of human retina (Clontech, Palo Alto, Calif.) was grown in *E. coli* Y 1090, expressed as described by Ch. E. Thirkill et al., Arch. Ophthalmol. (1992), in press, and probed with high-titered antibody reactive with the retinal CAR antigen obtained by Vieira and Messing, Gene 19:259 (1982).

8 positive clones were isolated, and the insert from one of the clones was ligated into an M13 phage (Bethesda Research Laboratories, Gaithersburg, Md.) as described by Messing and Vieira, Gene 19:269 (1982), and to a 'Bluescript' plasmid (Stratagene Cloning Systems, La Jolla, Calif.) as described by Alting-Mees, M. A. and Short, Nucl. Acids Res.17(22):9494 (1988), to permit double and single strand, dual directional, dideoxy sequencing. Sequencing was performed by the method described by Sanger, Nicklen and Coulson, P.N.A.S.(USA)74:5463 (1977), and confirmed by Lark Sequencing Technologies Inc., Houston, Tex.

Example 2

Isolation and Sequence of the 23 Kd Human Retinal CAR Antigen cDNA

A clone of 1100 bp was selected from a human cDNA retina library obtained from Clontech, Palo Alto, Calif. 94303, which expressed an immunoreactive beta-galactosidase-rec-CAR-Ag fusion protein of approximately 140 kDa. This fusion protein was used to affinity purify antibodies of the patient's serum that have selective affinity for the CAR antigen.

Antibodies selectively binding the CAR antigen from the same patient's serum were affinity purified using the β-galactosidase rec-CAR-Ag fusion protein. The thus isolated antibodies were then reapplied to Western blots of polypeptides expressed from a whole retina cDNA library as described by Olmsted (Olmsted, J. B., J. Biol. Chem. 235:11955 (1981)). The affinity-purified antibodies recognized only the CAR antigen and showed no reactivity with other retinal components when assayed either at high and low concentrations.

When the original CAR patient's serum was assayed on a Western blot of polypeptides expressed from a retina cDNA library, they recognized the 23 kDa retinal CAR antigen and additional retinal polypeptides. Dilutions of up to about 1:2,000, and sometimes greater may be utilized and the CAR antigen will bend the serum antibodies of the patients.

The cloned 1100 bp nucleotide sequence contains an open reading frame (ORF) of 229 codons beginning at position 1 and extending through position 687.

The primary nucleotide sequence of the human CAR cDNA and the 200 codon re-CAR-Ag ORF are shown below in Table 3. The sequence was determined utilizing both single strand and double strand DNA templates to obtain a complete sequence of both strands of the cDNA fragment. The major restriction sites are E: Eco RI; P: Pst I; and K: Kpn I. The DNA sequence is shown below in Table 3.

TABLE 3 cDNA Seguence

| | | | | | | | | | | | | | | |
|---|---|---|---|---|---|---|---|---|---|---|---|---|---|---|
| | | | 10 | | | 20 | | | 30 | | | | 40 | |
| | * | | * | | * | | * | | * | | * | | * | * |
| GAA | TTC | CGG | GCC | CAG | CCT | GCG | GCC | AGG | GGA | CCA | CGC | ACG | TCC | CAC |
| | 50 | | | 60 | | | | 70 | | | 80 | | | 90 |
| | * | | * | * | | * | | * | * | | * | | * | * |
| CCA | CCC | AGC | GAC | TCC | CCA | GCC | GCT | GCC | CAC | TCT | TCC | TCA | CTC | ATG |

TABLE 3-continued cDNA Sequence

| | | | | | | | | | | | | | | |
|---|---|---|---|---|---|---|---|---|---|---|---|---|---|---|
| | | | | | | | | | | | | | | Met |
| | | | 100 | | | 110 | | | 120 | | | | 130 | |
| | * | | * | * | | * | | * | * | | * | | * | * |
| GGG | AAC | AGC | AAA | AGT | GGG | GCC | CTG | TCC | AAG | GAG | ATC | CTG | GAG | GAG |
| Gly | Asn | Ser | Lys | Ser | Gly | Ala | Leu | Ser | Lys | Glu | Ile | Leu | Glu | Glu |
| | 140 | | | 150 | | | | 160 | | | 170 | | | 180 |
| PstI | | | * | * | | * | | * | * | | * | | * | * |
| CTG | CAG | CTG | AAC | ACC | AAG | TTC | TCG | GAG | GAG | GAG | CTG | TGC | TCC | TGG |
| Leu | Gln | Leu | Asn | Thr | Lys | Phe | Ser | Glu | Glu | Glu | Leu | Cys | Ser | Trp |
| | | | 190 | | | 200 | | | 210 | | | | 220 | |
| KpnI | * | | * | * | | * | | * | * | | * | | * | * |
| TAC | CAG | TCC | TTC | CTG | AAG | GAC | TGT | CCC | ACC | GGC | CGC | ATC | ACC | CAG |
| Tyr | Gln | Ser | Phe | Leu | Lys | Asp | Cys | Pro | Thr | Gly | Arg | Ile | Thr | Gln |
| | 230 | | | 240 | | | | 250 | | | 260 | | | 270 |
| | * | | * | * | | * | | * | * | | * | | * | * |
| CAG | CAG | TTC | CAG | AGC | ATC | TAC | GCC | AAG | TTC | TTC | CCG | ACA | CCG | ACC |
| Gln | Gln | Phe | Gln | Ser | Ile | Tyr | Ala | Lys | Phe | Phe | Pro | Thr | Pro | Thr |
| | | | 280 | | | 290 | | | 300 | | | | 310 | |
| | * | | * | * | | * | | * | * | | * | | * | * |
| CCC | AAG | GCC | TAC | GCC | CAG | CAT | GTG | TTC | CGC | AGC | TTC | GAT | TCC | AAC |
| Pro | Lys | Ala | Tyr | Ala | Gln | His | Val | Phe | Arg | Ser | Phe | Asp | Ser | Asn |
| | 320 | | | 330 | | | | 340 | | | 350 | | | 360 |
| | * | | * | * | | * | | * | * | | * | | * | * |
| CTC | GAC | GGC | ACC | CTG | GAC | TTC | AAG | GAG | TAC | GTC | ATC | GCC | CTG | CAC |
| Leu | Asp | Gly | Thr | Leu | Asp | Phe | Lys | Glu | Tyr | Val | Ile | Ala | Leu | His |
| | | | 370 | | | 380 | | | 390 | | | | 400 | |
| | * | | * | * | | * | | * | * | | * | | * | * |
| ATG | ACC | ACC | GCG | GGC | AAG | ACC | AAC | CAG | AAG | CTG | GAG | TGG | GCC | TTC |
| Met | Thr | Thr | Ala | Gly | Lys | Thr | Asn | Gln | Lys | Leu | Glu | Trp | Ala | Phe |
| | 410 | | | 420 | | | | 430 | | | 440 | | | 450 |
| | * | | * | * | | * | | * | * | | * | | * | * |
| TCC | CTC | TAC | GAC | GTG | GAC | GGT | AAC | GGG | ACC | ATC | AGC | AAG | AAT | GAA |
| Ser | Leu | Tyr | Asp | Val | Asp | Gly | Asn | Gly | Thr | Ile | Ser | Lys | Asn | Glu |
| | | | 460 | | | 470 | | | 480 | | | | 490 | |
| | * | | * | * | | * | | * | * | | * | | * | * |
| GTG | CTG | GAG | ATC | GTC | ATG | GCT | ATT | TTC | AAA | ATG | ATC | ACT | CCC | GAG |
| Val | Leu | Glu | Ile | Val | Met | Ala | Ile | Phe | Lys | Met | Ile | Thr | Pro | Glu |
| | 500 | | | 510 | | | | 520 | | | 530 | | | 540 |
| | * | | * | * | | * | | * | * | | * | | * | * |
| GAC | GTG | AAG | CTC | CTT | CCA | GAC | GAT | GAA | AAC | ACG | CCG | GAA | AAG | CGA |
| Asp | Val | Lys | Leu | Leu | Pro | Asp | Asp | Glu | Asn | Thr | Pro | Glu | Lys | Arg |
| | | | 550 | | | 560 | | | 570 | | | | 580 | |
| | * | | * | * | | * | | * | * | | * | | * | * |
| GCC | GAG | AAG | ATC | TGG | AAG | TAC | TTT | GGA | AAG | AAT | GAT | GAT | GAT | AAA |
| Ala | Glu | Lys | Ile | Trp | Lys | Tyr | Phe | Gly | Lys | Asn | Asp | Asp | Asp | Lys |
| | 590 | | | 600 | | | | 610 | | | 620 | | | 630 |
| | * | | * | * | | * | | * | * | | * | | * | * |
| CTT | ACA | GAG | AAA | GAA | TTC | ATT | GAG | GGG | ACA | CTG | GCC | AAT | AAG | GAA |
| Leu | Thr | Glu | Lys | Glu | Phe | Ile | Glu | Gly | Thr | Leu | Ala | Asn | Lys | Glu |
| | | | 640 | | | 650 | | | 660 | | | | 670 | |
| | * | | * | * | | * | | * | * | | * | | * | * |
| ATT | CTG | CGA | CTG | ATC | CAG | TTT | GAG | CCT | CAA | AAA | GTG | AAG | GAA | AAG |
| Ile | Leu | Arg | Leu | Ile | Gln | Phe | Glu | Pro | Gln | Lys | Val | Lys | Glu | Lys |
| | 680 | | | 690 | | | | 700 | | | 710 | | | 720 |
| | * | | * | * | | * | | * | * | | * | | * | * |
| ATG | AAG | AAC | GCC | TGA | TGC | CAA | CTG | TTC | AGC | TCT | CCT | CCC | TCC | ACC |
| Met | Lys | Asn | Ala | End | | | | | | | | | | |
| | | | 730 | | | 740 | | | 750 | | | | 760 | |
| | * | | * | * | | * | | * | * | | * | | * | * |
| TAC | CAC | TCA | CAT | GAC | ACC | CGT | GAG | CGC | CTG | TGC | ACA | CAC | ACA | CAC |
| | 770 | | | 780 | | | | 790 | | | 800 | | | 810 |
| | * | | * | * | | * | | * | * | | * | | * | * |
| ATG | CAC | ACA | CAC | GCG | CGC | GCA | CAC | ACA | CAC | ACA | CAC | ATC | CAC | CCC |
| | | | 820 | | | 830 | | | 840 | | | | 850 | |
| | * | | * | * | | * | | * | * | | * | | * | * |
| AGG | GCC | AAG | AGA | AAG | GCC | TGC | ACA | CAA | GCC | CAC | AGC | ACA | GCT | CCC |
| | 860 | | | 870 | | | | 880 | | | 890 | | | 900 |
| | * | | * | * | | * | | * | * | | * | | * | * |
| TGC | CAA | ACT | GAA | GCA | TCT | GTA | GTG | ACC | CAC | TGG | TTC | CTT | CTT | CCT |
| | | | 910 | | | 920 | | | 930 | | | | 940 | |
| | * | | * | * | | * | | * | * | | * | | * | * |
| GGG | TCT | TCA | GCA | TTC | CCT | CCC | ATC | ATG | CCC | GGT | CCC | ACC | CCT | CCC |
| | 950 | | | 960 | | | | 970 | | | 980 | | | 990 |
| | * | | * | * | | * | | * | * | | * | | * | * |
| TCT | GTC | CAC | CAG | CCA | TGG | CCC | TGT | GCT | AAT | CCC | AGG | ATT | AGG | CCA |
| | | | 1000 | | | 1010 | | | 1020 | | | | 1030 | |
| | * | | * | * | | * | | * | * | | * | | * | * |

TABLE 3-continued

| cDNA Sequence | | | | | | | | | | | | | | |
|---|---|---|---|---|---|---|---|---|---|---|---|---|---|---|
| TAG | GAG | TCC | TAA | GTG | TCA | CCC | CGC | TGT | AAG | CTC | CTT | TGT | GGA | GTG |
| | 1040 | | | 1050 | | | | 1060 | | | 1070 | | | 1080 |
| | * | | * | * | | * | | * | * | | * | | * | * |
| CTG | GGT | AAG | CAG | TTT | CCA | ATA | AAC | GCA | AGC | TGA | GCT | GGA | AAA | AAA |
| | | | 1090 | | | 1100 | | | | | | | | |
| | * | | * | * | | * | | | | | | | | |
| AAA | AAA | AAA | AAC | CGG | AAT | TC (SEQ. ID No:3) | | | | | | | | |

This ORF is in the same reading frame as the beta-galactosidase gene in the lambda gt11 vector. Based on this, the synthesis of a beta-galactosidase fusion protein approximately 18 Kd larger than native beta-galactosidase can be predicted. This is consistent with the observed 140 Kd size of the immunoreactive fusion protein. The ORF must be in the same reading frame as the amino acid dequence because it is being expressed as the antigen in the middle of the β-galactosidase gene. When the expression of the β-galactosidase gene is tripped with IPTG, the whole complex is then translated. The end product is the 22 Kd β-galactosidase enzyme with the 18 Kd CAR gene inserted in the middle: the 140 Kd fusion product described in this invention.

The 200 ORF codon that starts at the first Met codon (position 88-90) and continues through position 687 encodes the predicted polypeptide (designated rec-CAR-Ag). This polypeptide has extensive sequence homology with the bovine protein recoverin (Dizhoor, A.M., et al, Science 251:915 (1991)). The 23 Kd human CAR antigen differs at only 23 of 201 residues from bovine recoverin.

The correspondence of the human retinal CAR antigen to the published sequence of bovine recoverin is shown in Table 4 below. The two differ in about 23 amino acids located in two specific areas. These areas are the calcium binding sites on the CAR antigen molecule and are probably the most important parts of its sequence.

TABLE 4

Variant Fragments of h CAR and b Recoverin

```
                           10                   20                   30                   10
                           *                    *                    *                    *
HuCAR   MGNSKSGALSKEILEELQLNTKFSEEELCSWYQSFLKDCP   40
BoRec   -----------------------T-----S----------

                       [En**nn**nO*o*og*

                           50                   60                   70                   80
                           *                    *                    *                    *
HUCAR   TGRITQQQFQSIYAKFFPDTDPKAYAQHVFRSFDSNLDGT   80
BoRec   S-----R-E--T--S-----GA------------------

    I O**On**nn**n]        [En**nn**nO*O*OG*IO**

                           90                   100                  110                  90
                           *                    *                    *                    *
HUCAR   LDFKEYVIALHMTTAGKTNQKLEWAFSLYDVDGNGTISKN   120
BoRec   -------------S--------------------------

    On**nn**n]

                           130                  140                  150                  160
                           *                    *                    *                    *
HUCAR   EVLEIVMAIFKMITPEDVKLLPDDENTPEKRAEKIWKYFG   160
BoRec   -------------S---T-H--E--------------GF--

                           170                  180                  190                  200
                           *                    *                    *                    *   200
HuCAR   KNDDDKLTEKEFIEGTLANKEILRLIQFEPQKVKEKMKNA   (■)
BoRec   -K-------------------------------L-DKK  (□)
```

(■): (SEQ. No. 4)
(□): (SEQ. No. 5)

The CAR antigen was localized by histochemical studies to the inner segments and nuclei of rods and cones and to the region of the outer plexiform layer where cone pedicles and rod spherules are found.

This localization is similar to that reported for bovine recoverin (Dizhoor, A. M., et al (1991), supra).

Example 3

Preparation of Recombinant CAR Antigen

The recombinant form of the retinal CAR antigen (rec-CAR-Ag) was prepared by the IPTG-triggered expression of the recombinant human CAR gene in liquid lysates of lambda gt11 isolates, replicating in the *E. coli* host Y-1090 (e. g., Persson, M.A.A., et al., P.N.A.S. 88:2432 (1991).

Example 4

Affinity Purification of Antibodies Selectively Binding to Human Retinal CAR Antigen Repeated Western blot (20 cm) transfers of liquid lysates conducted as described by Olmstead, J. B., (1981) supra, allowed the resolution of the rec-CAR-Ag to be resolved by antibody reaction as a single band on nitrocellulose sheets as described by Olmstead, J. B., (1981), supra. 10 strips identified by human CAR serum as containing the antigen were excised and used repeatedly to isolate related antibodies from whole sera obtained from CAR patients, according to the method described by Olmstead, J. B. (1981), supra.

Example 5

Western Blot Assays

Side-by-side Western blot assays were performed with bovine retina and liquid lysates expressing the recombinant 23 Kd human CAR protein as described by Thirkill (Thirkill et al, Arch. Ophthalmol. 105:372 (1987)). These assays showed that the two antigens were binding to the same antibodies. That is, that antibodies that were affinity purified with the 140 Kd fusion protein reacted with the 23 Kd retinal CAR antigen on Western blots of whole bovine retina.

Example 6

Immunohistochemistry

A CAR patient's antibodies were affinity purified with the rec-CAR-antigen as described above. Deparaffinized sections of rhesus monkey retina were exposed for 1 hour at room temperature to the affinity purified antibodies. All antibody-antigen interactions were visualized using avidin-biotin conjugated to horse radish peroxidase reacting on diaminobenzidine (Vector laboratories, Burlingame, Calif.).

The invention now being fully described, it will be apparent to one of ordinary skill in the art that many changes and modifications can be made thereto without departing from the spirit or scope of the invention asset forth herein.

What is claimed as novel in Letters Patent of the United States is:

1. A substantially homogeneous, isolated polypeptide comprising the amino acid sequence as set forth in SEQ ID NO: 1.

2. The polypeptide of claim 1, wherein said polypeptide is obtained by transforming a nucleic acid encoding the polypeptide into a host cell, culturing the host cell under conditions that would allow expression of the polypeptide, and isolating the polypeptide.

* * * * *